US011534338B2

(12) United States Patent
Chabrier et al.

(10) Patent No.: US 11,534,338 B2
(45) Date of Patent: Dec. 27, 2022

(54) SYSTEM FOR LASER PHOTOCOAGULATION OF THE RETINA

(71) Applicants: QUANTEL MEDICAL, Cournon-d'Auvergne (FR); OFFICE NATIONAL D'ETUDES ET DE RECHERCHES AEROSPATIALES (ONERA), Palaiseau (FR)

(72) Inventors: Christian Chabrier, La Roche Blanche (FR); Serge Meimon, Chatillon (FR); Patrice Gayot, Cournon d'Auvergne (FR); Cyril Petit, Verrieres le Buisson (FR); Pedro Baracal De Mece, Neuilly-sur-Seine (FR); Benjamin Wassmer, Cournon-d'Auvergne (FR)

(73) Assignees: QUANTEL MEDICAL, Cournon-d'Auvergne (FR); OFFICE NATIONAL D'ETUDES ET DE RECHERCHES AEROSPATIALES (ONERA), Palaiseau (FR)

( * ) Notice: Subject to any disclaimer, the term of this patent is extended or adjusted under 35 U.S.C. 154(b) by 0 days.

(21) Appl. No.: 17/050,673

(22) PCT Filed: Apr. 25, 2019

(86) PCT No.: PCT/FR2019/050974
§ 371 (c)(1),
(2) Date: Oct. 26, 2020

(87) PCT Pub. No.: WO2019/207253
PCT Pub. Date: Oct. 31, 2019

(65) Prior Publication Data
US 2021/0228409 A1    Jul. 29, 2021

(30) Foreign Application Priority Data
Apr. 27, 2018    (FR) .................................... 1853721

(51) Int. Cl.
*A61F 9/008*    (2006.01)
(52) U.S. Cl.
CPC ............................. *A61F 9/00823* (2013.01); *A61F 2009/00863* (2013.01); *A61F 2009/00885* (2013.01)
(58) Field of Classification Search
CPC ............ A61F 2009/00863; A61F 2009/00865
See application file for complete search history.

(56) References Cited

U.S. PATENT DOCUMENTS 7,118,216 B2 *  10/2006  Roorda ................ A61B 3/1025
                                                    351/205
2004/0233388 A1 *  11/2004  Artsyukhovich ... A61F 9/00821
                                                    351/216

(Continued)

FOREIGN PATENT DOCUMENTS

WO    WO-9958047 A1 * 11/1999  ........... A61B 3/1025
WO    WO 2014/013438 A1    1/2014

OTHER PUBLICATIONS

French Search Report and Written Opinion for French Application No. 1853721, dated Nov. 29, 2018.

(Continued)

*Primary Examiner* — Mallika D Fairchild
*Assistant Examiner* — Shreya Anjaria
(74) *Attorney, Agent, or Firm* — Birch, Stewart, Kolasch & Birch, LLP

(57) ABSTRACT

The invention relates to a system for laser photocoagulation of the retina, comprising: a photocoagulation laser (1); an optical path (5) connecting the upstream photocoagulation laser (1) to a downstream laser outlet opening (6) intended to be positioned in front of the retina; an adaptive optical element (9) positioned in the optical path and configured to modify the wavefront of the laser beam being propagated in the optical path, in order to compensate for aberrations of the eye that occur as far as the retina; a position control loop (10)

(Continued)

Figure 1:
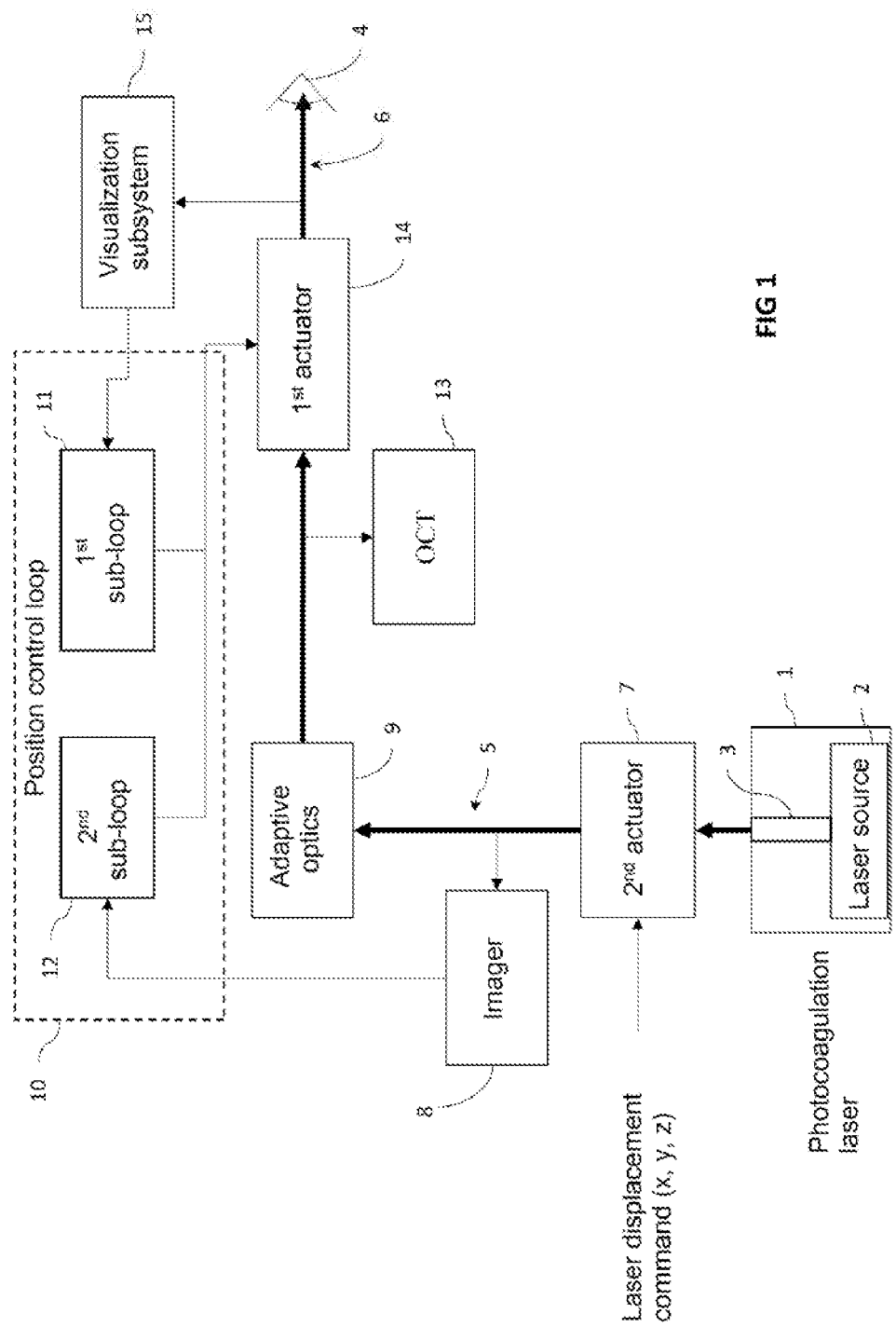

controlling a first actuator (14) positioned in the optical path downstream of the adaptive optical element in order to control the position of the laser outlet opening relative to the retina to be treated; and at least one imaging device (8) configured to obtain an image of the retina diverted from the optical path.

14 Claims, 2 Drawing Sheets

(56) References Cited

U.S. PATENT DOCUMENTS

| | | | | |
|---|---|---|---|---|
| 2007/0252951 | A1* | 11/2007 | Hammer | A61B 3/103 351/221 |
| 2011/0160622 | A1* | 6/2011 | McArdle | A61F 9/00825 606/4 |
| 2015/0202083 | A1* | 7/2015 | Takeda | A61B 18/20 606/4 |
| 2016/0270656 | A1* | 9/2016 | Samec | A61B 3/0025 |
| 2019/0365569 | A1* | 12/2019 | Skovgaard | A61B 90/20 |

OTHER PUBLICATIONS

International Search Report and International Written Opinion of the International Searching Authority (PCT/ISA/210) for International Application No. PCT/FR2019/050974, dated Sep. 30, 2019.

\* cited by examiner

SYSTEM FOR LASER PHOTOCOAGULATION OF THE RETINA

TECHNICAL FIELD OF THE INVENTION

The present invention belongs to the field of ophthalmology. More specifically, the invention relates to a system for laser photocoagulation of a retina.

Macular edema is a quite common retinal disorder characterized by one of an edema of the central region of the retina (macula) related to abnormalities of small blood vessels, resulting in reduced visual acuity. Macular edema is the main manifestation of diabetic retinopathy, which is the leading cause of blindness before age 55. The standard treatment for these macular edemas consists in performing a photocoagulation of these vessels in the central area of the retina with a laser. Other diseases may also benefit from the photocoagulation of the macula, such as retinal vein occlusions.

During a photocoagulation, the therapeutic target of the laser may be located at two layers:
- the layer of the retinal blood vessels, in the case of a localized edema. In this case, the edema is caused by a vascular dilation called a macroaneurysm on an identified retinal vessel, and a direct photocoagulation of the involved vessel is carried out;
- the retinal pigment epithelium, in the case of diffuse edema. One solution then consists in stimulating the absorbing function of the pigment epithelium, by photocoagulating it with repeated impacts.

These two layers of the retina are separated by a hundred microns, and are surrounded by other layers corresponding to functional tissues that must be preserved, at the risk of causing permanent loss of vision.

Until now, the surgeon operating the laser only had a two-dimensional visualization of the retina with a slit lamp, seen from the front, on which the surgeon relies to localize the point of laser impact on the surface of the retina, and dose the power of the laser: it is recommended to apply the laser until observing a discreet whitening with the slit lamp. It therefore appears that in the current surgical procedures, the focusing and the dosage of the laser are very empirical. Indeed, standard treatment procedures are not very reproducible from one practitioner to another.

In addition, during the operation, the eye is more or less stabilized with a contact lens held on the eye, which filters only partially the continual involuntary fixing movements of the eye. As a result, the laser impact may not correspond to the aimed position on the ocular fundus image obtained by the slit lamp.

To overcome this lack of accuracy in the localization of the laser impact, the current systems are configured to generate a large-sized laser impact, in order to ensure that the photocoagulation completely covers the area to be treated. The large size of the laser impact is obtained by delivering a broad laser beam, with a lateral diameter of the focal spot on the retina ranging from 100 µm to 500 µm, and having a small optical aperture, with longitudinal extension (in depth) of the focal spot on the retina of about 300 µm.

Furthermore, a large-sized laser impact also allows overcoming various ocular aberrations reducing the accuracy of the localization of the laser impact. Indeed, a real human eye is not strictly stigmatic, that is to say the image of a point is not a strictly clear point. These ocular aberrations can be static, the most common examples being vision defects corrected by glasses (myopia, hypermetropia, astigmatism, etc.). Aberrations can also be dynamic, for example caused by micro-accommodations of the crystalline lens, the tear film flow and the eye movements. These aberrations result in a Point Spread Function (PSF) which deviates from that of a theoretical perfect eye, and which varies rapidly over time.

The large size of the current laser impacts is not adapted to the size of the areas to be treated. By way of example, the macroaneurysms have sizes varying typically between 100 µm and 300 µm, even though the laser impact has a diameter of about 300 µm, not to mention the thermal scattering occurring around the laser impact area. As a result, lesions appear in the healthy tissues surrounding the area to be treated. However, the layer of the retinal blood vessels and the retinal pigment epithelium are surrounded by functional tissues whose deterioration can lead to permanent loss of vision.

PRESENTATION OF THE INVENTION

The invention aims at proposing a system for laser photocoagulation of a retina allowing accurate localization of the laser impact, both on the surface of the retina and in depth, and containing this laser impact in a restricted area, typically smaller than 100 µm, in order to limit the damage to healthy tissues in the vicinity of the area to be treated.

To this end, a system for laser photocoagulation of a retina is proposed, comprising:
- a photocoagulation laser comprising a laser source and an optical transport fiber,
- an optical path connecting the upstream photocoagulation laser to a downstream laser output intended to be placed in front of the retina, a laser beam emitted by the photocoagulation laser being intended to propagate along the optical path, wherein the laser source is a laser source configured to emit in a wavelength comprised between 520 nm and 690 nm in the optical fiber, and in that the optical transport fiber has a core with a diameter less than 50 µm, the system further comprising:
- an adaptive optics positioned in the optical path and configured to modify the wavefront of the laser beam propagating in the optical path in order to compensate ocular aberrations occurring up to the retina,
- a position control loop controlling a first actuator positioned in the optical path downstream of the adaptive optics to servo-control the position of the laser output with respect to the retina to be treated,
- at least one imager configured to acquire an image of the retina derived from the optical path.

The system is advantageously completed by the following characteristics, taken atone or in any one of their technically possible combination:
- a diameter of the laser beam at the pupil plane of the laser output 6 is comprised between 4 mm and 8 mm;
- a beam angle at the laser output is less than 5°;
- the control loop comprises two control sub-loops:
  - a first control sub-loop comprising a first imager configured to receive an image of the retina derived from the optical path downstream of the first actuator according to a first acquisition field,
  - a second control sub-loop comprising a second imager configured to receive an image of the retina derived from the optical path upstream of the adaptive optics according to a second acquisition field.
- the first field has a field angle at least twice as great as a field angle of the second field, and/or the second control sub-loop operates at a frequency greater than a frequency of the first sub-loop;

the system further comprises a visualization subsystem configured to receive an image of the retina derived from the optical path downstream of the first actuator and acquire images according to the first field;

the system further comprises a second actuator placed upstream of the adaptive optics, configured to receive a laser displacement command, and to act on the path of the laser beam in order to move the laser impact in three distinct directions in space;

the system is configured so that the second actuator moves the path of the laser beam while the photocoagulation laser emits the laser beam, such that the laser impact on the retina moves between several locations in a continuous manner;

the second actuator comprises:
  a scanner positioned in the optical path and adapted to perform a displacement of the laser beam in a focal plane perpendicular to the propagation of the laser beam, and
  a connector positioned in the optical path and movable in controlled translation in the direction of the laser beam;

the imager comprises a camera configured to acquire an image of the retina derived from the optical path upstream of the adaptive optics, the camera being movable in controlled translation in the direction of propagation of the light received by said camera;

the adaptive optics comprises:
  a correcting element, disposed on the optical path,
  a processing module configured to control the correcting element based on an analysis of a wave surface of the light traveling over the optical path;

the analysis of the wave surface is provided from a wave front sensor configured to receive light from the optical path upstream of the correcting element and to determine a measurement representative of a shape of a wave surface of the light traveling along the optical path, or the imager comprises a camera configured to acquire an image of the retina derived from the optical path upstream of the adaptive optics, or the analysis of the wave surface is provided from an image acquired by the imager comprising a camera configured to acquire an image of the retina derived from the optical path upstream of the adaptive optics;

the system comprises an optical coherence tomography device connected to the optical path downstream of the adaptive optics;

the laser source is a single-mode fiber laser source.

PRESENTATION OF THE FIGURES

Figure 2:
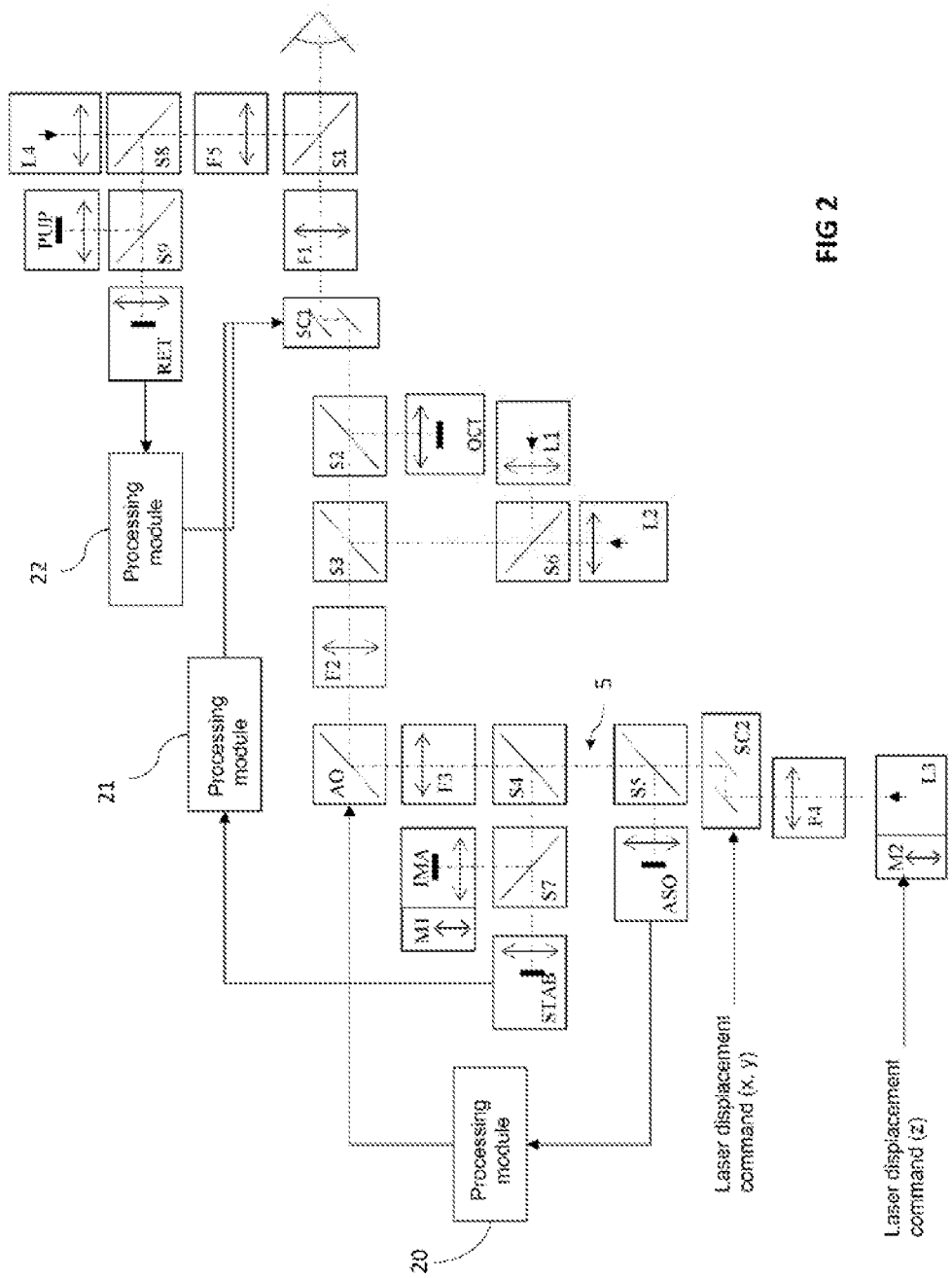

The invention will be better understood, thanks to the description below, which relates to embodiments and variants according to the present invention, given by way of non-limiting, examples and explained with reference to the appended schematic drawings, in which:

FIG. 1 schematically illustrates the main components of a system for laser photocoagulation of a retina according to one embodiment;

FIG. 2 illustrates a configuration in accordance with the one illustrated in FIG. 1.

DETAILED DESCRIPTION

With reference to FIG. 1 which schematically represents the main functional elements of the system, the system for laser photocoagulation of a retina comprises a photocoagulation laser 1 comprising a laser source 2 and an optical transport fiber 3. The laser source 2 is preferably a fiber laser source, that is to say whose amplifying medium is created in a rare-earth doped optical fiber. This optical fiber has a core diameter of preferably less than 12 µm, and more preferably less than 8 µm, such as for example 6 µm. The laser source 2 is said to be single-mode source that is to say with a parameter $M^2$ less than 1.5, and preferably less than 1.2. The single-mode aspect and the small diameter of the optical fiber of the laser source 2 allows obtaining a low coupling loss (less than 30%) during the transmission of the laser beam in the optical transport fiber 3 of the photocoagulation laser 1.

The laser source 2 is configured to emit in a wavelength comprised between 520 nm and 690 nm in the optical transport fiber 3, and preferably in a wavelength comprised between 540 nm and 630 nm, and more preferably between 550 nm and 600 nm. The laser source 2 is configured to emit a laser beam having sufficient power to cause photocoagulation of the targeted area of the retina 4, and in particular to cause the required thermal effect. For example, the laser beam can have a power comprised between 50 mW and 3 000 mW.

The optical transport fiber 3 receives the laser beam emitted by the laser source 2 and allows this laser beam to propagate in a non-recti linear fashion over a long distance without risk. The optical transport fiber 3 thus allows spatial decoupling between the photocoagulation laser 1 and the rest of the system, and therefore allows moving the laser source several meters from the retina 4. The optical transport fiber 3 has a core diameter of less than 50 µm, and preferably less than 25 µm, more preferably less than 15 µm, such as for example 12.5 µm. As a result, this transport fiber 3 can be spatially single-mode or slightly multimode. Preferably, the transport fiber 3 has a parameter $M^2$ less than 1.5, and preferably less than 1.2.

Furthermore, it is the output of this optical transport fiber 3 of the photocoagulation laser 1 that is imaged through the rest of the system on the patient's retina. The small diameter of the optical transport fiber 3 results in a small-dimensioned focal point, improving the containment of the laser impact. Thus, the system is characterized by a diameter of the laser beam at the pupil plane (that is to say at the position where the patient's pupil is positioned) of the laser output 6 comprised between 4 mm and 8 mm. Preferably, the system is also characterized by a low numerical aperture at the laser output 8. The numerical aperture in the air corresponds to the sine of the half aperture angle, which is the angle between the optical axis and the ray furthest from the optical axis, also called beam angle. Preferably, this beam angle is less than 5°, preferably 2.5°, more preferably 0.5°, or even more preferably less than 0.1°.

In the presence of an eye, the incident laser beam is focused by the crystalline lens of the eye towards the retina, which constitutes the focal plane. The crystalline lens acts like a lens converging the incident rays towards the retina. This convergence is better as the incident rays are parallel to the optical axis. A low numerical aperture at the laser output 6 results in a laser beam at the entrance of the eye, and therefore incident to the crystalline lens, practically collimated, and therefore by a quasi-punctual focusing at the retina. Conversely, a high numerical aperture at the laser output 6 would result in imperfect focusing by the crystalline lens, leading to an extended spot.

In addition, inside the eye, the laser beam that crossed the crystalline lens can also be characterized by an ocular numerical aperture as it converges towards the retina. This ocular numerical aperture depends in particular on the diameter of the beam and on the reciprocal of the focus of the eye. With a diameter of the laser beam at the pupil plane of the laser output 6 comprised between 4 mm and 8 mm, instead of about t mm for the systems of the state of the art, a large ocular numerical aperture is ensured. In addition, the fact that the laser beam incident on the pupil is collimated ensures good focusing on the retina.

However, the lateral resolution (perpendicular to the direction of propagation of the beam, in x, y) of the laser impact defined by the focal spot on the retina is proportional (for a perfect eye with circular aperture) to the reciprocal of the ocular numerical aperture, while the depth extension is proportional to the square of the reciprocal of the ocular numerical aperture. As a result, the high ocular numerical aperture allows limiting the dispersion of the laser beam at the focal spot on the retina, and therefore containing the laser impact. Furthermore, both lateral resolution and depth extension are proportional to the wavelength. The choice of a low wavelength (less than 690 nm, preferably less than 650 nm, and more preferably less than 600 nm) allows further improving this containment.

However, this tow containment of the impact needs to overcome the defects of the systems of the state of the art, which were hidden by the large size of their focal spot, and particularly the need to compensate the ocular aberrations for the laser, improve the accuracy of the localization and allow a fine visualization of the location of the laser impact both in lateral extension and in depth. To do so, the system has an optical path 5 provided with various elements which will now be described. Generally, the laser beam emitted by the photocoagulation laser 1 propagates in an optical path 5 defined by the system and connecting the upstream photocoagulation laser 1 to a downstream laser output 6, intended to be placed in front of the retina 4.

There are on this optical path 5:
an adaptive optics 9 positioned in the optical path 5 and configured to modify the wavefront of the laser beam propagating in the optical path 5 in order to compensate ocular aberrations occurring up to the retina 4,
a position control loop 10 controlling a first actuator 14 positioned in the optical path downstream of the adaptive optics in order to servo-control the position of the laser output 6 with respect to the retina 4 to be treated,
at least one imager 8 configured to acquire an image of the retina 4 derived from the optical path 5.

With reference to FIG. 2, an illustrative example is described below, whose different elements can intervene in various configurations as desired, which are described from downstream of the optical path to upstream. It is of course understood that various modifications could be made to the arrangement of the constituent elements of the system. The system comprises a downstream laser output 6, intended to be placed in front of the retina 4. A first beam splitter S1 on the optical path 5 allows deriving from the optical path an image of the retina 4. In the description, a beam splitter allows part of an incident light ray to pass while reflecting another part in another direction, and can be of any type, such as for example a half mirror.

There is, upstream of this first beam splitter S1, a shaping lens F1 that allows in particular reducing the field angle, for example to values comprised between 15° and 25°, by choosing the appropriate equivalent focal length. A scanner SC1 constituting the first actuator 14 allows controlling the displacement of the light beam in the optical path relative to the retina 4. The first actuator 14 allows scanning the entire central area of the retina, in particular because of the field angle which is still quite large.

Upstream of the first actuator 14 formed by the first scanner SC1, the optical path 5 includes a beam splitter S2 which allows deriving an image of the retina 4 towards an optical coherence tomography OCT device, which is therefore connected to the optical path 5 by this beam splitter S2. There is also on the optical path 5 a beam splitter S3 that allows entering illumination fight in the optical path 5. Alter another shaping len F2, there is a correcting element AO of the adaptive optics 9.

The optical path 5 then includes upstream a shaping lens F3, then a beam splitter S4 used to derive from the optical path 5 an image of the retina towards one or more imagers, upstream of the adaptive optics 9. Another beam splitter S5 on the optical path S5 allows deriving Sight from the optical path 5 to a wave front sensor ASO.

The optical path 5 then comprises a second actuator 7 placed upstream of the adaptive optics, configured to receive a laser displacement command, and to act on the laser beam to move the laser impact in three distinct directions in space. More specifically, it is an actuator 7 for three-dimensionally scanning the laser, making if possible to move the laser impact at the retina 4 at least in the direction of propagation of the laser, noted z, but also in a plane perpendicular to the direction of propagation of the laser, defined by two distinct directions noted x and y.

To do so, the second actuator 7 comprises, as illustrated in FIG. 2, a scanner SC2 positioned in the optical path and adapted to carry out a displacement of the laser beam in a focal plane (x, y) perpendicular to the propagation of the laser beam, and a connector L3 positioned in the optical path 5 and movable in controlled translation in the direction of the laser beam. The connector L3 makes the junction between the optical transport fiber 3 and the optical path 5. The laser beam emitted by the photocoagulation laser 1 passes from the optical transport fiber 3 to the optical path 5 via this connector L3, which can therefore be considered as a source for the downstream elements. The scanner SC2 acts for example by modifying the respective orientations of two mirrors facing each other, thus angularly shifting the laser beam that emerges therefrom.

The connector L3 is mounted on a motorized stage M2 receiving a laser displacement command and moving according to this command. The displacement of the connector L3 along the optical path 5 causes a modification of its focus plane, which is reflected along the optical path 5 to result in moving the focal plane at the laser output 6, that is to say the focus of the retina to be treated, in the direction of propagation of the laser beam. The user can thus finely modify the depth treated by the laser impact, and for example modify this depth when it is observed that the laser impact would affect functional tissues. This fine depth adjustment is all the more useful, due to the strong containment of the laser impact obtained by the system, as the depth of a laser impact no longer necessarily covers the entire area to be treated, and in that it can be necessary to carry out two laser impacts at different depths to treat the entire area to be treated.

In the case illustrated by FIG. 2, the scanner SC2 is placed downstream of the connector L3. However, it would be possible to invert their order. Furthermore, FIG. 2 shows the presence of a tens F4 which is present for the shaping of the laser beam at the outlet of the connector L3. Its diameter and its focal length are chosen to allow the path of laser beam satisfactorily between the constituent elements of the system. The disposition and the characteristics of this lens F4 are therefore left to the appreciation of those skilled in the art, as are those of the other tenses F1, F2 and F3.

The adaptive optics 9 is formed of several elements. As mentioned above, the adaptive optics 9 comprises a corrector element AO, used to correct the wavefront of the laser beam. This correction to be made to the wavefront is determined by means of a sensor placed upstream of the correcting element AO, and configured to receive light from the optical path 5 whose nature depends on the chosen configuration.

In the example illustrated by FIG. 2, the configuration of the adaptive optics 9 is called "Shack-hartmann", and comprises a wavefront sensor ASO, configured to receive tight from the optical path 5. In the illustrated case, the light is derived by means of the beam splitter S5 placed on the optical path 5. The wavefront sensor ASO determines a measurement representative of a shape of a wave surface of the Sight traveling along the optical path 5. More specifically, the wavefront sensor ASO decomposes a wavefront into elementary wave fronts and allows determining for each elementary wave front its orientation. The measurement of these orientations allows, after integration, leading back to the shape of the wave front.

Other configurations are possible. In particular, it is possible to provide for an adaptive optics without a dedicated sensor, by exploiting for example the imager 8 configured to acquire an image of the retina 4 derived from the optical path 5. The analysis of the wave surface is then made directly on the image obtained by this imager 8.

As explained above, the propagation of light in the eye reveals ocular aberrations which generate defects in this light, and particularly as regards its wave front. To better detect these alterations of the wavefront, a light source L1, associated with a lens, emits a light whose beam is similar to the one emitted by a point source, of small extent. Preferably, this light has wavelengths comprised between 600 nm and 700 nm, in particular because this range highlights the main aberrations, and is preferably still monochromatic. This light is returned by a beam splitter S6 to the optical path 5, more specifically to the beam splitter S3 already mentioned, and reaches the eye via the laser output 6. An artificial point source is thus created on the retina 4, which re-emits through scattering in all directions. The backscattered luminous flux propagates through the eye, then the optical path 5 up to the wavefront sensor ASO, which analyzes it in a pupil plane and determines the wavefront deformations, representative of the ocular aberrations.

The measurements from the wavefront sensor ASO are received and processed by a processing module 20, preferably a real-time computer, configured to receive the measurement from the wavefront sensor, and control the correcting element AO based on the measurement of the wavefront sensor, in order to compensate for the disturbances detected, in the typical case where the correcting element AO is a deformable mirror, the processing module 20 calculates the commands (for example voltages or intensities) to be sent to the deformable mirror, also placed in a pupil plane. The surface of the deformable mirror then changes to compensate the measured wavefront deformations.

The action of the correcting element therefore allows compensating the deformations for all the luminous fluxes arriving from the retina 4, such as for example those intended for imagers placed upstream of the correcting element, but also allows pre-modifying the luminous fluxes arriving from the upstream of the correcting element intended for the retina 4. These pre-mod if led luminous fluxes then have deformations opposite to those they undergo during their path towards the retina 4 so that, by reaching the retina 4, the ocular aberrations are compensated. Consequently, the light coming from the photocoagulation laser 1 has, at the laser impact on the retina 4, a much improved quality and accuracy. Particularly, the containment of the laser impact is improved.

The correction provided by the adaptive optics also benefits the imagers disposed upstream of the correcting element AO. Therefore, the system also comprises an imager 8 configured to acquire an image of the retina 4 derived from the optical path 5, upstream of the adaptive optics 9. Preferably, the imager 8 is movable in controlled translation in the direction of propagation of the light received by the imager 8. To do so, the imager 8 comprises an imaging camera IMA mounted on a motorized stage M1 which allows, depending on received commands, moving this imaging camera IMA. The beam splitter S4 allows deriving part of the luminous flux traveling through the optical path 5 towards the imaging camera IMA, which allows obtaining a two-dimensional image of the area of the retina facing the output 6 at a given focus depth. As mentioned above, the imaging camera IMA can be used for the analysis of the wave surface that allows controlling the correcting element AO of the adaptive optics 9 in a configuration without a dedicated wavefront sensor.

By means of the motorized stage M1, the imaging camera IMA can be moved to modify the focus depth at the retina 4. It is then possible to image the retina at different depths, indeed, due to the significant containment of the laser obtained by means of the system, the depth of a laser impact no longer necessarily covers the entire area to be treated. The only information of the location of the laser impact is no longer sufficient. It is then preferable to be able to make an imaging at different depths so that the user can visualize the extent in depth of the area to be treated or of the area already treated.

The imager 8 can comprise, instead of the imaging camera IMA or in addition, a camera STAB, called stabilization camera, for acquiring an image of the retina 4 derived from the optical path 5, upstream of the adaptive optics 9. This stabilization camera STAB is used to implement a regulation to servo-control the position of the laser output 6 with respect to the retina 4 to be treated, in the example illustrated in FIG. 2, the imager 8 comprises a stabilization camera STAB and an imaging camera IMA. A beam splitter S7 receiving from the optical path 5 part of the luminous flux circulating therein by means of the beam splitter S4 allows supplying these two cameras with light. The imager 8 is very upstream of the optical path, and requires great accuracy. At this stage, the field angle may have been reduced by the various crossed lenses F1, F2, F3 to a value less than 5°.

A light source L2 is provided for the illumination of the retina for the imager 8, that is to say here for the stabilization camera STAB and/or the imaging camera IMA. This light source L2 preferably emits in a wavelength comprised between 800 nm and 900 nm. The light emitted by this light source passes through the beam splitter S6 it shares with the light source L1 then meets the optical path 5 via the beam splitter S3. The emitted light meets the retina 4, and the light coming from the illuminated retina 4 goes up the optical path 5 via the adaptive optics 9. The images acquired by the imager 8 thus benefit from the correction provided by the adaptive optics 9.

The imager 8 upstream of the adaptive optics 9 is therefore used to implement a position regulation of the laser output 6 with respect to the retina 4. More specifically, it is the output of the stabilization camera STAB that is used. The camera STAB transmits acquired images to a processing module 21, preferably a real-time computer which, from these images, determines a command of the first actuator 14 to move the light beam in the optical path relative to the retina 4 in order to stabilize the position of the light beam, in particular by compensating the involuntary movements of the eye. The processing module 21 can for example exploit an image of the photoreceptors and a correlation-type algorithm to determine the movements of the retina 4, and determine a command of the first actuator 14 so that the light beam follows these movements.

Thus, the first actuator 14 is controlled by the control loop 10 to servo-control the position of the laser output 6 with respect to the retina 4 to be treated. However, another measurement can be used to control the first actuator 14. Preferably, the control loop 10 determines a command of the first actuator 14 as a function, on the one hand, of a first measurement derived from the optical path 5 downstream of the first actuator 14 and, on the other hand, of a second measurement derived from the optical path 5 upstream of the first actuator 14. If this second measurement comes from the imager 8, the first measurement comes from a large-field visualization subsystem, downstream of the first actuator 14.

The first beam splitter S1, placed downstream of the optical path 4, allows obtaining a wide visualization of the retina 4, exploited by a large-field visualization subsystem 15. The field angle can then typically be greater than 30°. The visualization subsystem 15 can be used both to acquire images Intended for the user, to servo-control the position of the first actuator 14, and to project on the retina a fixation target which can serve as a visual cue.

This visualization subsystem 15 comprises a light source and lens L4 assembly emitting in a wide wavelength band, typically over a major part of the visible spectrum. The luminous flux thus emitted meets the optical path 5 by the first beam splitter S1, via another beam splitter S8 and a shaping lens F5. This luminous flux then illuminates the retina 4 in order to allow imaging the retina 4, in the other direction, the luminous flux coming from the retina 4 is derived from the optical path 5 by the first beam splitter S1, passes into the shaping lens F5; and is deviated by the beam splitter S8 in the direction of the visualization imagers. Another beam splitter S9 allows directing the flux towards two visualization imagers: a pupil imager PUP, which allows acquiring and displaying the image of the pupil, and a retina imager RET, which allows acquiring and displaying the image of the retina. The retina imager RET allows implementing the position regulation of the scanner SC1 acting as a first actuator 14.

Thus, the control loop 10 comprises two control sub-loops. The first control sub-loop 11 comprises a first imager configured to receive an image of the retina derived from the optical path downstream of the first actuator 14 according to a first acquisition field. This first imager is the retina imager RET, and the first acquisition field is therefore the angle field greater than 30°. The images acquired by the retina imager RET are transmitted to a processing module 22, typically a real-time computer, which determines a command for the first scanner SC1.

A second control sub-loop 12 comprises the imager 8 configured to receive an image of the retina derived from the optical path upstream of the adaptive optics 9 according to a second acquisition field. It is the control sub-loop comprising the stabilization camera STAB and the processing module 21. Preferably, the first field has a field angle at least twice greater than a field angle of the second field, and preferably greater than 10*. For example, if the first acquisition field is the angle field greater than 30°, the second acquisition field has an angle less than 15°, and preferably less than 10°. As the acquisition field is defined by the used imager, in the case presented above, the second acquisition field has an angle less than 5°, like that of the imager 8.

Preferably, also, the second control sub-loop 12 operates at a frequency greater than the frequency of the first sub-loop 11. For example, the first sub-loop 11 can operate with a frequency less than 100 Hz, or even less at 75 Hz, for example of 60 Hz, while the second sub-loop 12 can operate with a frequency greater than 150 Hz, for example 200 Hz. The first sub-loop 11 can thus be designated as a large-field or low-frequency loop, and the second sub-loop 12 as a small-field or high-frequency loop.

It should be noted that the different control modules 20, 21, 22 can be combined together or in pairs, and it is possible for example that their respective functions are fulfilled by a single computer, preferably real-time computer. In addition, the system can comprise a visualization screen to which are sent the images acquired by the imagers such as the imager PUP, the camera IMA or the optical coherence tomography OCT device, so that the user of the system can visualize them.

Preferably, the optical coherence tomography OCT device is synchronized with other imagers in order to match the images acquired by the optical coherence tomography OCT device with the images acquired by another imager. This means that acquisition parameters of the optical coherence tomography OCT device are related to acquisition parameters of other imagers. Preferably, the image acquired by the optical coherence tomography OCT device is synchronized on the image of the retina obtained by the other imagers. This allows the user to be able to visualize the same area on the OCT image and on the other images. This also allows knowing the position of the laser shot on the OCT image.

Also preferably, the optical coherence tomography OCT device is configured to acquire an OCT image during the emission of the laser beam by the photocoagulation laser 1 so that the user can visualize in real time the effect of the laser beam on the retina 4. The different imagers of course also allow visualization after and before the laser impact.

Thanks to the system described above, the size of the laser impact remains small, being more contained than the previous systems, and the user can observe the laser impact in three dimensions and in real time. It is then possible to implement a displacement of the laser beam without interrupting it, in order to cover an area to be treated, unlike the prior systems in which several distinct laser impacts were made, the point of laser impact being moved between two emissions of the laser beam. It is also possible that the system is configured to emit the laser beam in a discontinuous manner, but whose discontinuity is not related to the displacement of the beam. Preferably, the system is configured so that the second actuator 7 moves the path of the laser beam while the photocoagulation laser 1 emits the laser beam, so that the laser impact on the retina moves between several locations in a continuous manner. The displacement of the laser beam is preferably carried out by the second actuator 7, but could alternatively or in addition be carried out by the first actuator 14.

The invention is not limited to the embodiment described and represented in the appended figures. Modifications remain possible, in particular from the point of view of the constitution of the various elements or by substitution of technical equivalents, without thereby departing from the scope of protection of the invention.

The invention claimed is:

1. A system for laser photocoagulation of a retina comprising:
   a photocoagulation laser comprising a laser source and an optical transport fiber,
   an optical path connecting a photocoagulation laser to a laser output to be placed in front of the retina, so that a laser beam emitted by the photocoagulation laser propagates along the optical path in a propagation direction, the propagation direction being oriented from the photocoagulation laser to the laser output, so that the photocoagulation laser is located upstream the laser output with respect to the propagation direction, said laser beam having a wavefront,
wherein the laser source is a laser source configured to emit in a wavelength comprised between 520 nm and 690 nm in the optical transport fiber, and the optical transport fiber has a core with adiameter less than 50 µm,
the system for laser photocoagulation comprising:
   an adaptive optics positioned in the optical path and configured to modify the wavefront of the laser beam propagating along the optical path in order to compensate ocular aberrations occurring up to the retina,
   an imager configured to acquire an image of the retina based on light transported from the retina to the imager, the light following the optical path from the laser output to an extraction point, the light exiting the optical path at the extraction point, the extraction point being located in the optical path downstream of the photocoagulation laser and upstream of the adaptive optics with respect to the propagation direction,
   a first actuator being different from the adaptive optics, the first actuator being positioned in the optical path downstream of the adaptive optics with respect to the propagation direction, said first actuator configured to control a position of the laser output with respect to the retina, and
   a position control loop controlling the first actuator to servo-control the position of the laser output with respect to the retina, on the basis of an image of the retina derived from the optical path and acquired by the imager.

2. The system according to claim 1, wherein a diameter of the laser beam at a pupil plane of the laser output is comprised between 4 mm and 8 mm.

3. The system according to claim 1, wherein a beam angle at the laser output is less than 5°.

4. The system according to claim 1, wherein the position control loop comprises two position control sub-loops:
   a first position control sub-loop comprising a first imager configured to receive an image of the retina derived from the optical path downstream of the first actuator according to a first acquisition field,
   a second position control sub-loop comprising a second imager configured to receive an image of the retina derived from the optical path upstream of the adaptive optics according to a second acquisition field.

5. The system according to claim 4, wherein the first acquisition field has a field angle at least twice as great as a field angle of the second acquisition field, and/or the second control sub-loop operates at a frequency greater than a frequency of the first sub-loop.

6. The system according to claim 4, further comprising a visualization subsystem configured to receive an image of the retina derived from the optical path downstream of the first actuator and acquire images according to the first acquisition field.

7. The system according to claim 1, further comprising a second actuator placed upstream of the adaptive optics, configured to receive a laser displacement command, and to act on a path of the laser beam in order to move a laser impact in the retina in three distinct directions in space.

8. The system according to claim 7, wherein the system is configured so that the second actuator moves the path of the laser beam while the photocoagulation laser emits the laser beam, such that the laser impact in the retina moves between several locations in a continuous manner.

9. The system according to claim 7, wherein the second actuator comprises:
   a scanner positioned in the optical path and adapted to perform a displacement of the laser beam in a focal plane perpendicular to the propagation of the laser beam, and
   a connector positioned in the optical path and movable in controlled translation in the propagation direction of the laser beam.

10. The system according to claim 1, wherein the imager comprises a camera configured to acquire an image of the retina derived from the optical path upstream of the adaptive optics, the camera being movable in controlled translation in the direction of propagation of the light received by said camera.

11. The system according to claim 1, wherein the adaptive optics comprises:
   a correcting element, disposed in the optical path, and
   a processing module configured to control the correcting element based on an analysis of a wave surface of a light traveling along the optical path.

12. The system according to claim 11, wherein the analysis of the wave surface is provided from a wavefront sensor configured to receive light from the optical path upstream of the correcting element and to determine a measurement representative of a shape of a wave surface of the light traveling along the optical path, or the imager comprises a camera configured to acquire an image of the retina derived from the optical path upstream of the adaptive optics, or the analysis of the wave surface is provided from an image acquired by the imager comprising a camera configured to acquire an image of the retina derived from the optical path upstream of the adaptive optics.

13. The system according to claim 1, comprising an optical coherence tomography device connected to the optical path downstream of the adaptive optics.

14. The system according to claim 1, wherein the laser source is a single-mode fiber laser source.

* * * * *